United States Patent
Yang et al.

(10) Patent No.: US 9,725,574 B2
(45) Date of Patent: Aug. 8, 2017

(54) POLYESTER-BASED PLASTICIZER FOR RESIN

(71) Applicant: CJ CHEILJEDANG CORPORATION, Seoul (KR)

(72) Inventors: Young Lyeol Yang, Goyang-si (KR); Ji Ho Hwang, Seoul (KR); Do Yong Shim, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/305,862

(22) PCT Filed: Mar. 18, 2015

(86) PCT No.: PCT/KR2015/002599
§ 371 (c)(1),
(2) Date: Nov. 18, 2016

(87) PCT Pub. No.: WO2015/163582
PCT Pub. Date: Oct. 29, 2015

(65) Prior Publication Data
US 2017/0066901 A1    Mar. 9, 2017

(30) Foreign Application Priority Data
Apr. 24, 2014 (KR) .................. 10-2014-0049555

(51) Int. Cl.
C08K 5/11 (2006.01)
C08L 67/00 (2006.01)
C08L 69/00 (2006.01)
C08L 101/00 (2006.01)
C07C 69/716 (2006.01)

(52) U.S. Cl.
CPC .............. C08K 5/11 (2013.01); C07C 69/716 (2013.01); C08L 67/00 (2013.01); C08L 69/00 (2013.01); C08L 101/00 (2013.01); C08K 2201/018 (2013.01)

(58) Field of Classification Search
CPC .... C08G 63/672; C07C 59/347; C07C 69/716
See application file for complete search history.

(56) References Cited

U.S. PATENT DOCUMENTS

| | | | |
|---|---|---|---|
| 5,173,301 A | * | 12/1992 | Itoh ................... A61L 24/046 424/445 |
| 5,290,852 A | | 3/1994 | Vyvoda |
| 6,127,512 A | | 10/2000 | Asrar et al. |
| 7,166,654 B2 | | 1/2007 | Fujita et al. |

FOREIGN PATENT DOCUMENTS

| | | |
|---|---|---|
| JP | 2003292474 A | 10/2003 |
| JP | 2005036104 A | 2/2005 |
| JP | 2006022268 A | 1/2006 |

OTHER PUBLICATIONS

International Search Report for International Application No. PCT/KR2015/002599 dated May 14, 2015.
Written Opinion for International Application No. PCT/KR2015/002599 dated May 14, 2015.

* cited by examiner

*Primary Examiner* — Paul A Zucker
(74) *Attorney, Agent, or Firm* — Cantor Colburn LLP

(57) ABSTRACT

The present disclosure provides a polyester-based plasticizer for resin, which is represented by Formula 1.

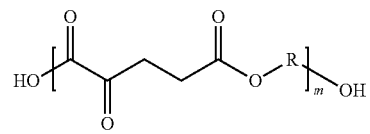

12 Claims, No Drawings

POLYESTER-BASED PLASTICIZER FOR RESIN

TECHNICAL FIELD

The present disclosure relates to a plasticizer for resin, and more particularly, to a polyester-based plasticizer for resin.

BACKGROUND ART

Polymer resins and plasticizers for polymer resins that are in common use in the plastic material field are mostly derived from petroleum origins and are widely used as packing materials such as various films.

In general, phthalate-based plasticizers including dibutyl phthalate (DBP) or dioctyl phthalate (DOP) are used in general-purpose resin such as polyvinyl chloride (PVC). However, phthalate-based plasticizers use sources obtained from petroleum, raising concern of harmful effects as toxic, endocrine-disrupting chemicals. For this reason, some countries are taking legal action to prevent use of phthalate-based plasticizers.

Research has been performed to develop environmentally friendly biodegradable polymer resin. As typical biodegradable polymer resin developed, polylactic acid is produced by polymerization of lactic acid derived from a biological organism. There also have been attempts to use polylactic acid as an alternative to conventional general-purpose polymer resin in various application fields, through development of biodegradable polymer resin, for example, by forming a copolymer of polylactic acid with other aliphatic hydrocarboxylic acids or by forming polyester through esterification of polylactic acid with aliphatic polyvalent alcohol.

However, polylactic acid that is stiff and inductile due to high crystallinity and rigid molecular structure is vulnerable to thermal decomposition during a process, and thus is not suitable for use alone in the packing field where flexibility of material is required. For a variety of applications of polylactic acid, also in the packaging material field, through softening of polylactic acid, adding a plasticizer to polylactic acid may be considered, though further research and development are required to soften the physical properties of polylactic acid with a plasticizer.

As a plasticizer for such polylactic acid, adipic acid ester may be used. However, adipic acid as a main source of ester polymer is also derived from petroleum origin raw material, and not environmentally friendly, and has a limited processability when used with polyester resin having poor mechanical properties in terms of tensile strength and impact resistance.

α-ketoglutaric acid is known as a product of deamination reaction of glutamate in biological organisms and an intermediate product of the Krebs cycle. In other words, α-ketoglutaric acid is attainable from biological organisms, but is difficult to be obtained via a petrochemical method, according to the prior art information.

DETAILED DESCRIPTION OF THE INVENTION

Technical Problem

The present disclosure provides an environmentally friendly plasticizer that is derived from biological organisms, having good processability to improve mechanical properties such as durability, tensile strength, and impact resistance of a resin composition.

Technical Solution

According to an aspect of the present disclosure, there is provided a polyester-based plasticizer for resin, represented by Formula 1:

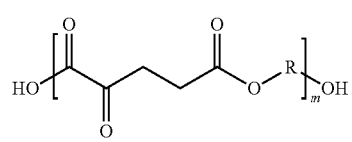

[Formula 1]

wherein, in Formula 1,

R is a linear or branched $C_2$-$C_{20}$ alkylene with 0 or more oxygen atom of ether group in the middle of the carbon chain thereof; and m is an integer from 1 to 20.

According to an aspect of the present disclosure, there is provided a polyester-based plasticizer comprising a plasticizer represented by Formula 1a or 1 b, or any combinations thereof:

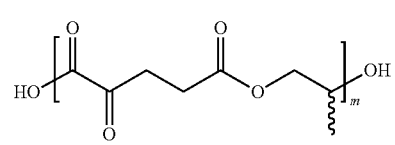

[Formula 1a]

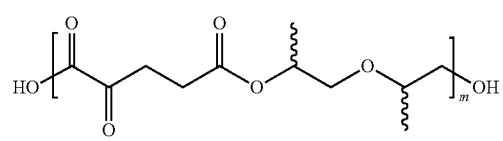

[Formula 1b]

wherein, in Formulae 1a and 1 b, m is defined the same as defined in Formula 1.

Advantageous Effects

As described above, according to the one or more embodiments, a polyester-based plasticizer prepared using α-ketoglutaric acid monomers that are derived from biological organisms may be environmentally friendly and may improve mechanical properties such as low tensile strength and impact resistance of a polyester resin when applied to the polyester resin. Therefore, a polyester-based plasticizer according to any of the embodiments may be used as an environmentally friendly alternative to conventional phthalate-based plasticizers raising concern of endocrine-disrupting chemicals.

BEST MODE

Hereinafter, embodiments of the present disclosure will be described in greater detail. Unless otherwise defined, all terms (including technical and scientific terms) used herein have the same meaning as commonly understood by one of ordinary skill in the art to which this disclosure belongs. Although exemplary methods or materials are listed herein, other similar or equivalent ones are also within the scope of the present disclosure. All publications disclosed as references herein are incorporated in their entirety by reference.

As a result of research into the development of an environmentally friendly plasticizer that may be derived from biological organisms, not petrochemically, and that has as good processability as conventional plasticizers to improve mechanical properties such as tensile strength and impact resistance of polymer resin, the present inventors obtained a polyester polymer using α-ketoglutaric acid monomers derived from a biological organism and identified that mechanical properties of resin in terms of durability, tensile strength, and impact resistance may be improved with the polyester polymer.

According to an aspect of the present disclosure, there is provided a polyester-based plasticizer for resin, represented by Formula 1:

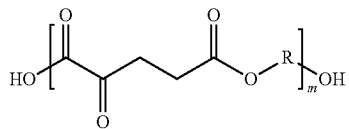

[Formula 1]

In Formula 1,

R may be a linear or branched $C_2$-$C_{20}$ alkylene with 0 or more oxygen atom of ether group in the middle of the carbon chain thereof; and m may be an integer from 1 to 20.

For example, the compound represented by Formula 1 may include a polyester-based plasticizer of Formula 1a or 1 b, or any combinations thereof. However, embodiments are not limited thereto.

According to an aspect of the present disclosure, there is provided a polyester-based plasticizer including a plasticizer represented by Formula 1a or Formula 1b, or any combinations thereof:

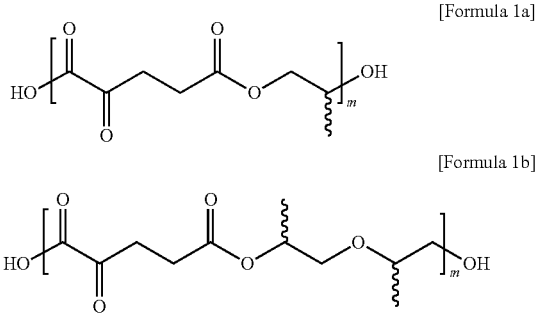

[Formula 1a]

[Formula 1b]

In Formulae 1a and 1 b, m may be defined the same as defined above in connection with Formula 1, and the wavy line means that the group may or may not be present.

In some embodiments, a polyester-based plasticizer according to any of the embodiments may be used for any resin, for example, as a plasticizer for biodegradable resin or general-purpose resin.

For example, the biodegradable resin may be at least one selected from the group consisting of poly-L-lactic acid (PLLA), poly-D-lactic acid (PDLA), stereocomplex-PLA (sc-PLA), polycaprolactone, polyglycolic acid, polycarbonate, and polybutylene succinate (PBS). However, embodiments are not limited thereto.

For example, the general-purpose resin may be at least one selected from the group consisting of polyvinyl chloride, polyethylene, polypropylene, acrylonitrile-butadiene-styrene (ABS) resin, and polystyrene. However, embodiments are not limited thereto.

Polylactic acid (PLA) as an environmentally friendly material derived from biological organism may be prepared by direct condensation polymerization (WO 2013/184014A1) or ring opening polymerization of lactide after synthesis of L-, D-, and meso-lactide from L-lactic acid and D-lactic acid (U.S. Pat. No. 5,770,682 A). L-, D-, and meso-lactide may have different thermal and physical characteristics depending on isomers. L-lactide and D-lactide with relatively high optical purity may have good thermal and physical characteristics, compared to meso-lactide. Normally, PLLA and PDLA are prepared from L- and D-lactide with high optical purity, respectively.

Stereocomplex-PLA (sc-PLA), which may be prepared by melt-blending PLLA and PDLA that are in the form of polymer resin through polymerization, may have good thermal and physical characteristics, compared to original PLLA and PDLA.

PLA as an environmentally friendly material derived from biological organisms is currently applicable to various materials, but may be thermally decomposed at a process temperature, with poor impact resistance due to poor flexibility after processing. PVC as a general-purpose resin may have strong cohesion due to strong intermolecular strength, be thermally decomposed at a fluid temperature or greater, and have poor impact resistance due to strong intermolecular chain strength and poor flexibility. As such, a variety of resins, including biodegradable resins and general-purpose resins as described above, have mechanical characteristics unsuitable for processing. To address these drawbacks of resins, plasticizers may be used. The polyester-based plasticizer of Formula 1 may improve the mechanical characteristics of a variety of resins as described above.

In particular, when a polyester-based plasticizer according to an embodiment of the present disclosure is added to a resin, a polar portion of the molecular chain of the resin may be solvated with a polar portion of the plasticizer. This may sterically prevent the molecular chains of the resin from being closer to one another and at the same time enable the micro-Brownian movement at low temperature of molecules in the molecular chains of the resin, consequentially improving flexibility and elasticity at room temperature of the resin.

In a polyester-based plasticizer according to any of the above-described embodiments, as a plasticizer including α-ketoglutaric acid monomers, one more ketone group per unit molecule may be present in a main chain of the polyester-based plasticizer, compared with other common polyester-based plasticizers, so that the polyester-based plasticizer may have increased polarity, and consequentially may be stably adsorbed within a main chain of a polymer resin that is mixed with the polyester-based plasticizer, with alkylene groups as a non-polar portion providing mobility, so that poor mechanical characteristics of the polymer resin in terms of flexibility and impact resistance may be improved by the polyester-based plasticizer applied to the polymer resin. The polyester-based plasticizer according to any of the above-described embodiments may be prepared using α-ketoglutaric acid monomers derived from a biological organism, and thus be environmentally friendly as an alternative to phthalate-based plasticizers raising concern of endocrine-disrupting chemicals.

The polyester-based plasticizer for resin, represented by Formula 1, according to any of the embodiments, may be prepared using a method that involves polyesterification of α-ketoglutaric acid with R(OH)$_2$, as illustrated in Reaction Scheme 1:

Next, a sample was prepared by blending about 10 parts to 20 parts by weight of the resulting polyester plasticizer with 100 parts by weight of a commercially available polylactic acid resin (INGEO 2003D, available from Nature-Works LLC).

[Reaction Scheme 1]

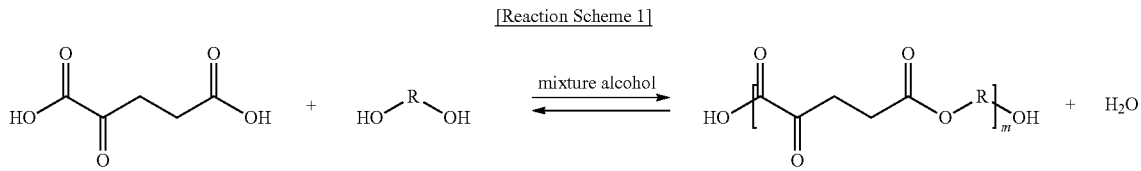

In Reaction Scheme 1, R and m may be defined the same as those defined in connection with Formula 1.

The composition of a mixture alcohol in Reaction Scheme 1 may be appropriately chosen based on the known knowledge in the organic chemistry field by one of ordinary skill in the art.

The polyesterification may be performed by stirring reactants and a mixture alcohol put into a reactor with a gradual temperature rise to about 170-210° C. under reflux at the same temperature. The polyesterification may be terminated when a target acid value is reached, followed by cooling, thereby preparing a polyester-based plasticizer of Formula 1. Specific conditions for the polyesterification are not limited to the above, and may be appropriately chosen based on the known knowledge in the organic chemistry field by one of ordinary skill in the art.

MODE OF THE INVENTION

One or more embodiments of the present disclosure will now be described in detail with reference to the following examples. However, these examples are only for illustrative purposes and are not intended to limit the scope of the one or more embodiments of the present disclosure.

Example 1: Preparation of Polyester Plasticizer and Application Thereof to Resin 1

α-ketoglutaric acid (55.9 wt %), 1,3-propanediol (36.1 wt %), and a mixture alcohol (7.3 wt %) were put into a flask equipped with a condenser, and then stirred with a gradual temperature rise to about 170-210° C. and maintained the temperature while stirring under reflux for polyesterification.

The polyesterification reaction was terminated when a target acid value was reached, followed by cooling to room temperature. The number average molecular weight (Mn) of a resulting polyester compound was measured by gel permeation chromatography (GPC).

The composition of the mixture alcohol used was as follows: 1-2% of C6 (hexyl), 40-42% of C8 (caprylic), 54-57% of C10 (decyl), a maximum of 1.0% of C12 (lauryl), a maximum of 1.0% of hydrocarbon, as analyzed by gas chromatography.

The resulting polyester plasticizer had a molecular weight (Mn) of 1893 (by GPC) and an acid value of 16.5 mg (KOH).

Example 2: Preparation of Polyester Plasticizer and Application Thereof to Resin 2

α-ketoglutaric acid (55.1 wt %), 1,2-propanediol (37.5 wt %), and a mixture alcohol (7.5 wt %) were put into a flask equipped with a condenser, and then stirred with a gradual temperature rise to about 170-210° C. and maintained the temperature while stirring under reflux for esterification.

The esterification reaction was terminated when a target acid value was reached, followed by cooling to room temperature. The number average molecular weight (Mn) of a resulting polyester plasticizer was measured by GPC.

The composition of the mixture alcohol used was as follows: 1-2% of C6 (hexyl), 40-42% of C8 (caprylic), 54-57% of C10 (decyl), a maximum of 1.0% of C12 (lauryl), a maximum of 1.0% of hydrocarbon, as analyzed by gas chromatography.

The resulting polyester plasticizer had a molecular weight (Mn) of 1812 (by GPC) and an acid value of 15.2 mg (KOH).

Next, a sample was prepared by blending about 10 parts to 20 parts by weight of the resulting polyester plasticizer with 100 parts by weight of a commercially available polylactic acid resin (INGEO 2003D, available from Nature-Works LLC).

Example 3: Preparation of Polyester Plasticizer and Application Thereof to Resin 3

α-ketoglutaric acid (56.2 wt %), 1,2-propanediol (35.7 wt %), and a mixture alcohol (7.2 wt %) were put into a flask equipped with a condenser, and then stirred with a gradual temperature rise to about 170-210° C. and maintained the temperature while stirring under reflux for esterification.

The esterification reaction was terminated when a target acid value was reached, followed by cooling to room temperature. The number average molecular weight (Mn) of a resulting polyester plasticizer was measured by GPC.

The composition of the mixture alcohol used was as follows: 1-2% of C6 (hexyl), 40-42% of C8 (caprylic), 54-57% of C10 (decyl), a maximum of 1.0% of C12 (lauryl), a maximum of 1.0% of hydrocarbon, as analyzed by gas chromatography.

The resulting polyester plasticizer had a molecular weight (Mn) of 1872 (by GPC) and an acid value of 16.1 mg (KOH).

Next, a sample was prepared by blending about 10 parts by weight of the resulting polyester plasticizer with 100 parts by weight of a commercially available polyvinyl chloride (PVC) resin (TH-1000, available from Taiyo Vinyl Corporation).

Comparative Example 1: Preparation of Adipic Acid Polyester Plasticizer and Application Thereof to Resin (1)

A polyester plasticizer including adipic acid monomers were prepared as follows. Adipic acid (57.5 wt %), 1,3-propanediol (34.2 wt %), and a mixture alcohol (7.1 wt %) were put into a flask equipped with a condenser, and then stirred with a gradual temperature rise to about 170-210° C. and maintained the temperature while stirring under reflux for polyesterification.

The esterification reaction was terminated when a target acid value was reached, followed by cooling to room temperature. The number average molecular weight (Mn) of a resulting polyester plasticizer was measured by GPC.

The composition of the mixture alcohol used was as follows: 1-2% of C6 (hexyl), 40-42% of C8 (caprylic), 54-57% of C10 (decyl), a maximum of 1.0% of C12 (lauryl), a maximum of 1.0% of hydrocarbon, as analyzed by gas chromatography.

The resulting polyester plasticizer had a molecular weight (Mn) of 1721 (by GPC) and an acid value of 13.4 mg (KOH).

Next, a sample was prepared by blending about 10 parts to 20 parts by weight of the resulting polyester plasticizer with 100 parts by weight of a commercially available polylactic acid resin (INGEO 2003D, available from NatureWorks LLC).

Comparative Example 2: Bare Resin without Plasticizer (1)

A commercially available polylactic acid (INGEO 2003D, available from NatureWorks LLC) as a biodegradable resin was used without a plasticizer.

Comparative Example 3: Preparation of Adipic Acid Polyester Plasticizer and Application Thereof Resin (2)

A polyester plasticizer including adipic acid monomers that are in common use were prepared as follows. Adipic acid (57.1 wt %), 1,3-propanediol (34.3 wt %), and a mixture alcohol (7.2 wt %) were put into a flask equipped with a condenser, and then stirred with a gradual temperature rise to about 170-210° C. and maintained the temperature while stirring under reflux for esterification.

The esterification reaction was terminated when a target acid value was reached, followed by cooling to room temperature. The number average molecular weight (Mn) of a resulting polyester plasticizer was measured by GPC.

The composition of the mixture alcohol used was as follows: 1-2% of C6 (hexyl), 40-42% of C8 (caprylic), 54-57% of C10 (decyl), a maximum of 1.0% of C12 (lauryl), a maximum of 1.0% of hydrocarbon, as analyzed by gas chromatography.

The resulting polyester plasticizer had a molecular weight (Mn) of 1695 (by GPC) and an acid value of 13.1 mg (KOH).

Next, a sample was prepared by blending about 10 parts by weight of the resulting polyester plasticizer with 100 parts by weight of a commercially available PVC resin (TH-1000, available from Taiyo Vinyl Corporation).

Comparative Example 4: Bare Resin without Plasticizer (2)

A commercially available PVC (TH-1000, available from Taiyo Vinyl Corporation) as a general-purpose resin was used without a plasticizer.

Experimental Example

Thermal characteristics such as a glass transition temperature (Tg) and a melting point (Tm) of the samples prepared in Examples 1 to 3 and Comparative Examples 1 to 4 were analyzed by differential scanning calorimetry (DSC) at about 10° C./min according to ASTM D3418.

Mechanical characteristics of the samples, including a tensile strength and an elongation, were measured according to ASTM D882 (Test samples prepared had a thickness of about 50 and a size of about 15 mm×75 mm).

TABLE 1

Results of physical properties analysis

| | Example 1 | | Example 2 | | Example 3 | Comparative Example 1 | Comparative Example 2 | Comparative Example 3 | Comparative Example 4 |
|---|---|---|---|---|---|---|---|---|---|
| Plasticizer content (wt %) | 10 | 20 | 10 | 20 | 10 | 10 | 20 | — | 10 | — |
| Tensile strength (MPa) | 32.1 | 35.2 | 39.7 | 43.1 | 55.2 | 28.3 | 28 | 47.8 | 54.3 | 56.5 |
| Elongation (%) | — | 181 | 10 | 205 | 309 | 13 | 210 | 3 | 321 | 83 |
| Tm (° C.) | 121.2 | 95.6 | 105.6 | 97.8 | 202.1 | 116.1 | 95 | 149 | 198.5 | 221 |
| Tg (° C.) | 43.4 | 37.2 | 43.1 | 35.6 | 73.5 | 43.5 | 34.4 | 6.1 | 76.6 | 80 |

Referring to Table 1, when mixed with a plasticizer according to an embodiment, the resins had a reduced glass transition temperature (Tg) that may ensure improved flexibility with reduced stiffness, and a reduced melting point (Tm) that may ensure a practically applicable process temperature and improved processability. Therefore, a polyester-based plasticizer according to any of the embodiments was found to be appropriate for packaging purpose.

When applied to a resin, a polyester-based plasticizer according to any of the embodiments is found to improve physical properties of the resin as good as those of resin when used together with a phthalate-based plasticizer raising concern of endocrine-disrupting chemicals.

While this disclosure has been particularly shown and described with reference to preferred embodiments thereof, it will be understood by those skilled in the art that various changes in form and details may be made therein without departing from the spirit and scope of the disclosure as defined by the appended claims. It is also to be appreciated that all changes and equivalents that do not depart from the spirit and technical scope of the present disclosure are encompassed in the present disclosure.

The invention claimed is:

1. A polymer composition comprising, a blend of a polymer resin and a polyester-based plasticizer for the polymer resin, wherein the polyester-based plasticizer comprises a compound of Formula 1:

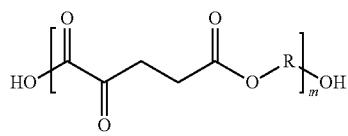

Formula 1 wherein, in Formula 1,
R is a linear or branched $C_2$-$C_{20}$ alkylene group, with 0 or more oxygen atom of an ether group distributed at different positions in the carbon chain thereof; and
m is an integer from 1 to 20.

2. A polymer composition comprising, a blend of a polymer resin and a polyester-based plasticizer for the polymer resin, wherein the polyester-based plasticizer comprises a compound of Formula 1a, Formula 1b, or a combinations thereof:

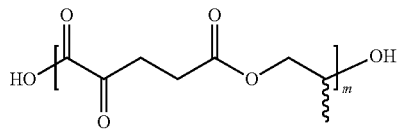

Formula 1a

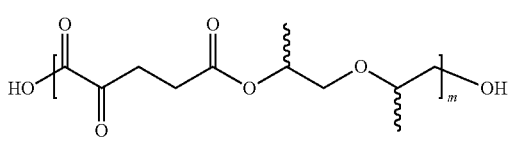

Formula 1b wherein, in Formulae 1a and 1b, m is defined the same as defined in claim 1, and the wavy line means that the group may or may not be present.

3. The polymer composition according to claim 1, wherein the polymer resin is a biodegradable polymer resin selected from the group consisting of poly-L-lactic acid (PLLA), poly-D-lactic acid (PDLA), stereocomplex-PLA (sc-PLA), polycaprolactone, polyglycolic acid, polycarbonate, and polybutylene succinate (PBS).

4. The polymer composition according to claim 1, wherein the polymer resin is a general-purpose polymer resin selected from the group consisting of polyvinyl chloride, polyethylene, polypropylene, acrylonitrile-butadiene-styrene (ABS) resin, and polystyrene.

5. The polymer composition according to claim 2, wherein the polymer resin is a biodegradable resin selected from the group consisting of poly-L-lactic acid (PLLA), poly-D-lactic acid (PDLA), stereocomplex-PLA (sc-PLA), polycaprolactone, polyglycolic acid, polycarbonate, and polybutylene succinate (PBS).

6. The polymer composition according to claim 2, wherein the polymer resin is a general-purpose resin selected from the group consisting of polyvinyl chloride, polyethylene, polypropylene, acrylonitrile-butadiene-styrene (ABS) resin, and polystyrene.

7. A method of increasing the plasticity of a blend of polymer resin using a polyester-based plasticizer of Formula 1:

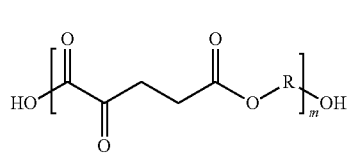

Formula 1 wherein, in Formula 1,
R is a linear or branched $C_2$-$C_{20}$ alkylene group, with 0 or more oxygen atom of an ether group distributed at different positions in the carbon chain thereof; and
m is an integer from 1 to 20.

8. A method of increasing the plasticity of a blend of polymer resin using a polyester-based plasticizer comprising a compound of Formula 1a, Formula 1b, or a combination thereof:

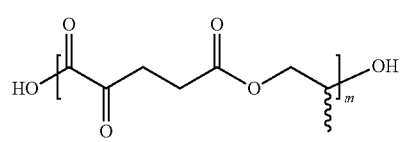

Formula 1a

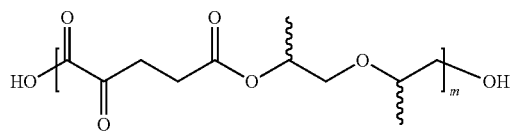

Formula 1b wherein, in Formulae 1a and 1b, m is an integer from 1 to 20, and the wavy line means that the group may or may not be present.

9. The method according to claim 7, wherein the polymer resin is a biodegradable polymer resin selected from the group consisting of poly-L-lactic acid (PLLA), poly-D-lactic acid (PDLA), stereocomplex-PLA (sc-PLA), polycaprolactone, polyglycolic acid, polycarbonate, and polybutylene succinate (PBS).

10. The method according to claim 7, wherein the polymer resin is a general-purpose polymer resin selected from the group consisting of polyvinyl chloride, polyethylene, polypropylene, acrylonitrile-butadiene-styrene (ABS) resin, and polystyrene.

11. The method according to claim 8, wherein the polymer resin is a biodegradable resin selected from the group consisting of poly-L-lactic acid (PLLA), poly-D-lactic acid (PDLA), stereocomplex-PLA (sc-PLA), polycaprolactone, polyglycolic acid, polycarbonate, and polybutylene succinate (PBS).

12. The method according to claim 8, wherein the polymer resin is a general-purpose resin selected from the group consisting of polyvinyl chloride, polyethylene, polypropylene, acrylonitrile-butadiene-styrene (ABS) resin, and polystyrene.

* * * * *